United States Patent
Ekvall et al.

(10) Patent No.: US 10,243,557 B2
(45) Date of Patent: Mar. 26, 2019

(54) WIRELESS OPHTHALMIC SURGICAL FOOTSWITCH

(71) Applicant: Novartis AG, Basel (CH)

(72) Inventors: Johan Gustaf Ekvall, Laguna Beach, CA (US); Paul J. Essex, Rancho Santa Margarita, CA (US); Kirk Wellington Todd, Lake Forest, CA (US)

(73) Assignee: Novartis AG, Basel (CH)

( * ) Notice: Subject to any disclaimer, the term of this patent is extended or adjusted under 35 U.S.C. 154(b) by 162 days.

(21) Appl. No.: 15/272,795

(22) Filed: Sep. 22, 2016

(65) Prior Publication Data

US 2018/0083621 A1    Mar. 22, 2018

(51) Int. Cl.
| | |
|---|---|
| *H02K 49/04* | (2006.01) |
| *H03K 17/975* | (2006.01) |
| *A61B 17/00* | (2006.01) |

(52) U.S. Cl.
CPC .. *H03K 17/975* (2013.01); *A61B 2017/00199* (2013.01); *A61B 2017/00221* (2013.01); *A61B 2017/00973* (2013.01)

(58) Field of Classification Search
USPC .......................................................... 307/125
See application file for complete search history.

(56) References Cited

U.S. PATENT DOCUMENTS

| | | | | |
|---|---|---|---|---|
| 7,781,941 B2 * | 8/2010 | Horvath | ................. | A61B 17/00 310/339 |
| 2004/0222468 A1 * | 11/2004 | DCamp | ................. | B81B 7/0038 257/355 |
| 2005/0164837 A1 * | 7/2005 | Anderson | ............ | A63B 22/001 482/52 |

\* cited by examiner

*Primary Examiner* — Rexford Barnie
*Assistant Examiner* — Xuan Ly

(57) ABSTRACT

Disclosed is a surgical footswitch, comprising a base, a pedal mounted to the base, and a variable air capacitor mechanically coupled to the pedal, such that movement of the pedal is operative to vary the capacitance of the variable air capacitor. The footswitch further comprises a capacitance-sensing controller circuit electrically connected to the variable air capacitor and configured to measure a capacitance of the variable air capacitor and to produce a control signal based on the measured capacitance, such that the control signal reflects a position of the pedal or a change in the position of the pedal, and a wireless interface electrically connected to the capacitance-sensing controller circuit and configured to wirelessly relay the control signal to a surgical console.

6 Claims, 5 Drawing Sheets

WIRELESS OPHTHALMIC SURGICAL FOOTSWITCH

TECHNICAL FIELD

The present disclosure relates generally to systems and methods for controlling a surgical system, and more particularly to a footswitch operable to control surgical systems.

BACKGROUND

During the use of a complex patient treatment apparatus or surgical system, for example, surgical equipment used when performing ophthalmic surgery, the control of a variety of different subsystems, such as pneumatic and electronically driven subsystems may be required. Typically, the operation of the subsystems is controlled by a microprocessor-driven console. The microprocessor controls within a surgical console receive mechanical inputs from either the operator of the surgical system or from an assistant. A control input device, such as a footswitch, is often used to accept mechanical inputs. These mechanical inputs originate from the movement of the foot of an operator to govern the operation of a subsystem within the patient treatment apparatus. The mechanical inputs from the movement of the foot of the operator are translated into electrical signals which are fed to the microprocessor controls. The electrical signals are then used to control the operational characteristics of a subsystem in a complex patient treatment apparatus.

Examples of footswitches include a foot pedal or tiltable treadle similar to the accelerator pedal used to govern the speed of an automobile. The movement of the foot pedal or tiltable treadle typically provides a linear control input. Such linear control inputs may be used, for example, for regulating vacuum, rotational speed, power, or reciprocal motion.

In more complex footswitch assemblies, side or wing switches may be added to housings on either side of the foot pedal in order to provide additional capabilities to the footswitch. The condition of these side or wing switches is changed by the application of pressure from the front portion of the operator's foot or from the rear portion of the operator's foot.

As these footswitches became more complex, the need to establish secure reliable communications between the footswitch and the surgical console resulted in a number of wired pathways that connect the footswitch and surgical console. As the footswitches are moved about the operating room, these tethers, wires and cables can become tangled with other equipment. Accidentally disconnecting these cables can result in improper control inputs that have the potential to injure a patient. To address these problems, U.S. Pat. No. 7,781,941, issued 24 Aug. 2010, disclosed a surgical footswitch that includes a base, a pedal, a capacitance-sensing controller circuit, a wireless interface, and an internal power generator. In this footswitch, the pedal mounts upon the base and pivots, and is coupled to the capacitance-sensing controller circuit. As the pedal pivots, the capacitance-sensing controller circuit translates the mechanical signal of the pedal into a control signal based on the pedals position and/or orientation. The wireless interface is coupled to the capacitance-sensing controller circuit to receive the control signal, and then couples the surgical footswitch to a surgical console operable to control and direct surgical equipment. This wireless interface eliminates the tangle of wires or tethers, which may be a hazard in the surgical theater. The internal power generator translates footswitch movement into stored energy to eliminate potential failures of the footswitch during a procedure and reduce the need to replace batteries within the footswitch.

Even with these improved footswitches, however, there remains a need for improved performance and, in particular, for extended battery life.

SUMMARY

Disclosed herein is an energy efficient footswitch that uses a novel sensing method and a zero-power-consumption tactile feedback scheme. Embodiments of the disclosed footswitch may use inexpensive, non-rechargeable, consumer batteries, while yielding greatly extended battery life.

An example surgical footswitch comprises a base, a pedal mounted to the base, and a variable air capacitor mechanically coupled to the pedal, such that movement of the pedal is operative to vary the capacitance of the variable air capacitor. The example footswitch further comprises a capacitance-sensing controller circuit electrically connected to the variable air capacitor and configured to measure a capacitance of the variable air capacitor and to produce a control signal based on the measured capacitance, such that the control signal reflects a position of the pedal or a change in the position of the pedal. The example still further comprises a wireless interface electrically connected to the capacitance-sensing controller circuit and configured to wirelessly relay the control signal to a surgical console.

In some embodiments, the surgical footswitch comprises first and second variable air capacitors mechanically coupled to the pedal, such that rotation of the pedal in a vertical plane is operative to vary the capacitance of the first variable air capacitor and movement of the pedal in a horizontal plane is operative to vary the capacitance of the first variable air capacitor. In these embodiments, the capacitance-sensing controller circuit is electrically connected to the first and second variable air capacitors and is configured to produce first and second control signals or a composite control signal based on the respective capacitances of the first and second variable air capacitors, and the wireless interface is configured to relay the first and second control signals to the surgical console.

In some embodiments, the surgical footswitch further comprises an eddy current brake mechanism mechanically coupled to the pedal, such that the movement of the pedal is operative to cause the eddy current brake mechanism to generate a mechanically resistive force opposing the movement. This eddy current brake mechanism may be a brushed direct-current (DC) motor, for example, and in some embodiments may be electrically coupled to an electrically variable load resistance.

In some embodiments, the surgical footswitch further comprises one or more non-rechargeable batteries configured to power the capacitance-sensing controller circuit. In some of these embodiments, the capacitance-sensing controller circuit further comprises a battery sense circuit configured to monitor a voltage level of the one or more non-rechargeable batteries, and the capacitance-sensing controller circuit is configured to relay a low-battery signal to the surgical console, via the wireless interface, responsive to detecting that the monitored voltage level is below a predetermined threshold level.

It is to be understood that both the foregoing general description and the following detailed description are exemplary and explanatory in nature, and are intended to provide an understanding of the presently disclosed techniques and apparatus without limiting the scope of those techniques and apparatus. In that regard, additional aspects, features, and advantages of the presently disclosed techniques and apparatus will be apparent to those skilled in the art from the following detailed description and the accompanying figures.

DETAILED DESCRIPTION

Figure 1:
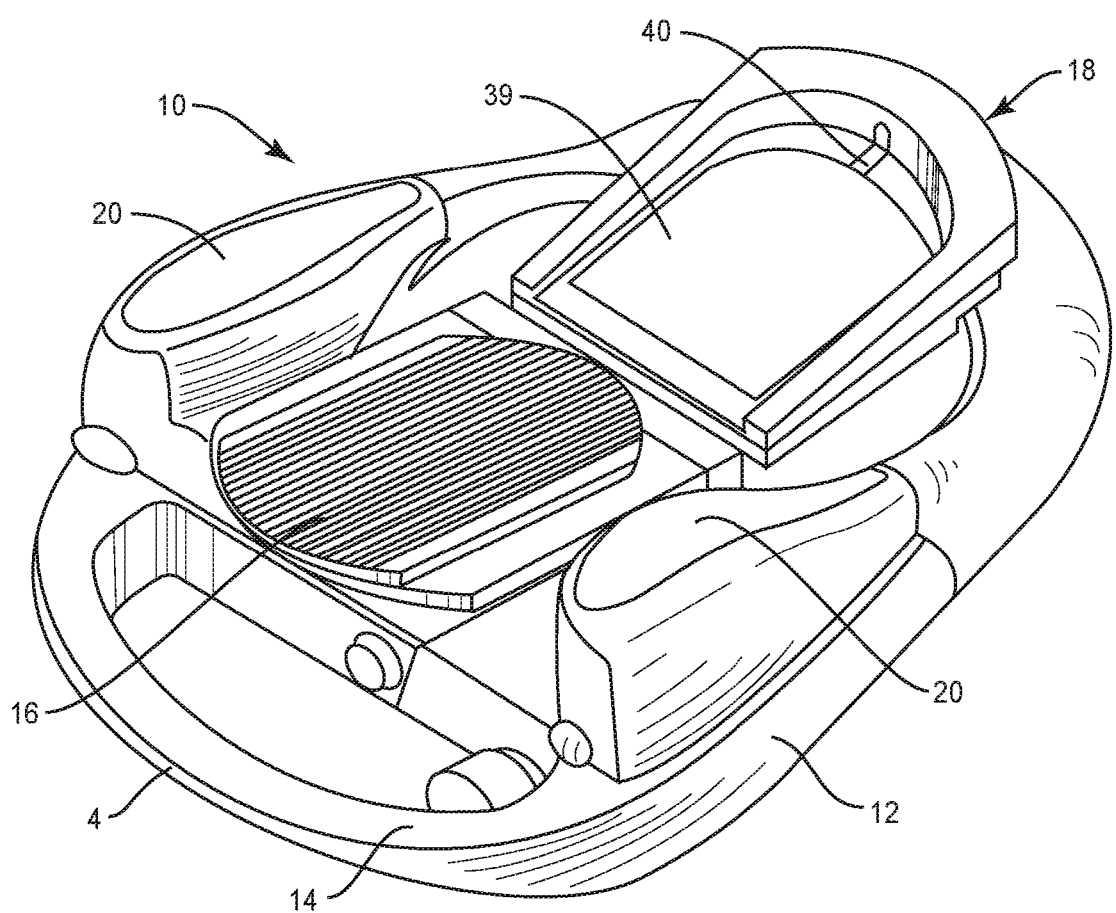
FIG. 1 depicts an example footswitch assembly.

For the purposes of promoting an understanding of the principles of the present disclosure, reference will now be made to the example embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

Current wireless footswitch implementations use a rechargeable battery system, due to the high amounts of current consumed by the footswitch treadle position sensing and tactile force feedback functions. With these implementations, the surgical staff must remember to place the footswitch on a charging stand or plug it into a charging cable after using the system. A failure to fully recharge the footswitch can result in an unintentional interruption of the surgery.

FIG. 1 depicts an embodiment of a footswitch assembly 10 that, as described in detail below, includes several features that can be used to reduce the power consumed by the treadle position sensing and tactile feedback functions. With careful design of the wireless link, together with the positioning sensing and tactile feedback approaches described below, the power consumed by the footswitch can be lowered to such a degree that inexpensive, non-rechargeable batteries may be used instead of rechargeable batteries, reducing the complexity and cost of the footswitch and eliminating the need for charging of the device.

Surgical footswitch assembly 10 includes a body or housing that further includes bottom housing 12 and top housing 14, and a foot pedal or treadle 16, all of which can be made from any suitable material, such as stainless steel, titanium or plastic. Other embodiments may additionally include a separate heel cup assembly 18 and a handle 4 positioned in the front. Side or wing switches 20 may be placed on the top of housing 14 on either side of the foot pedal 16.

Figure 2A:
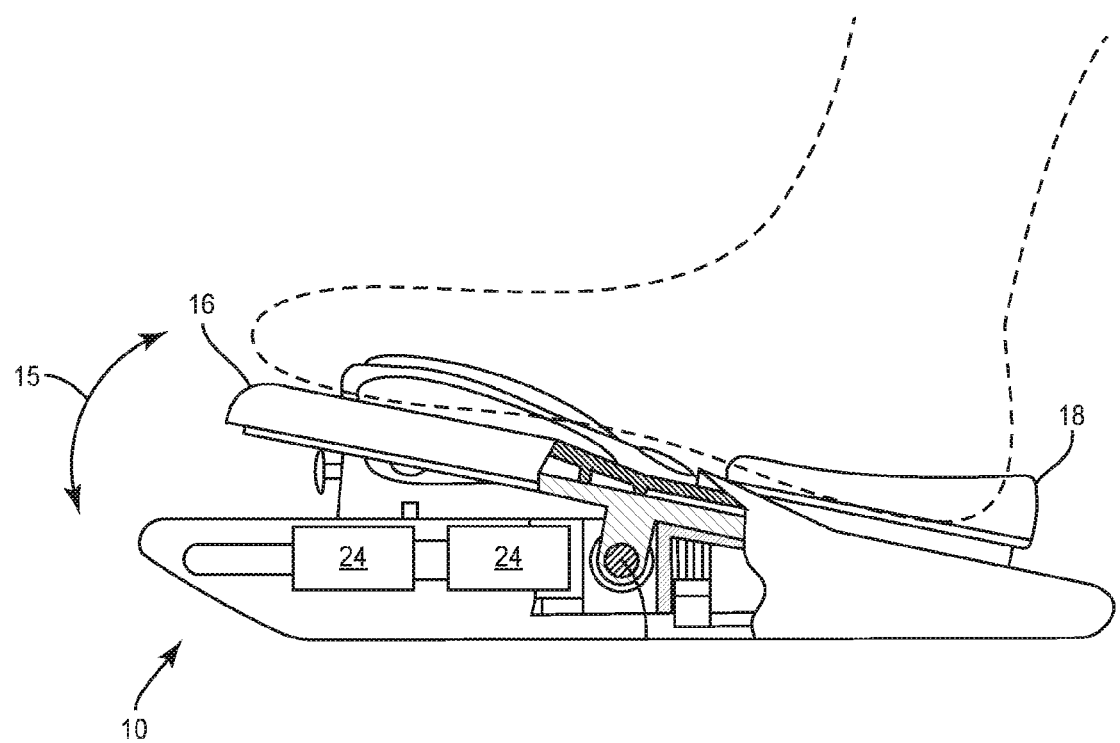
FIG. 2A provides a cross-sectional view of an example footswitch assembly.
Figure 2B:
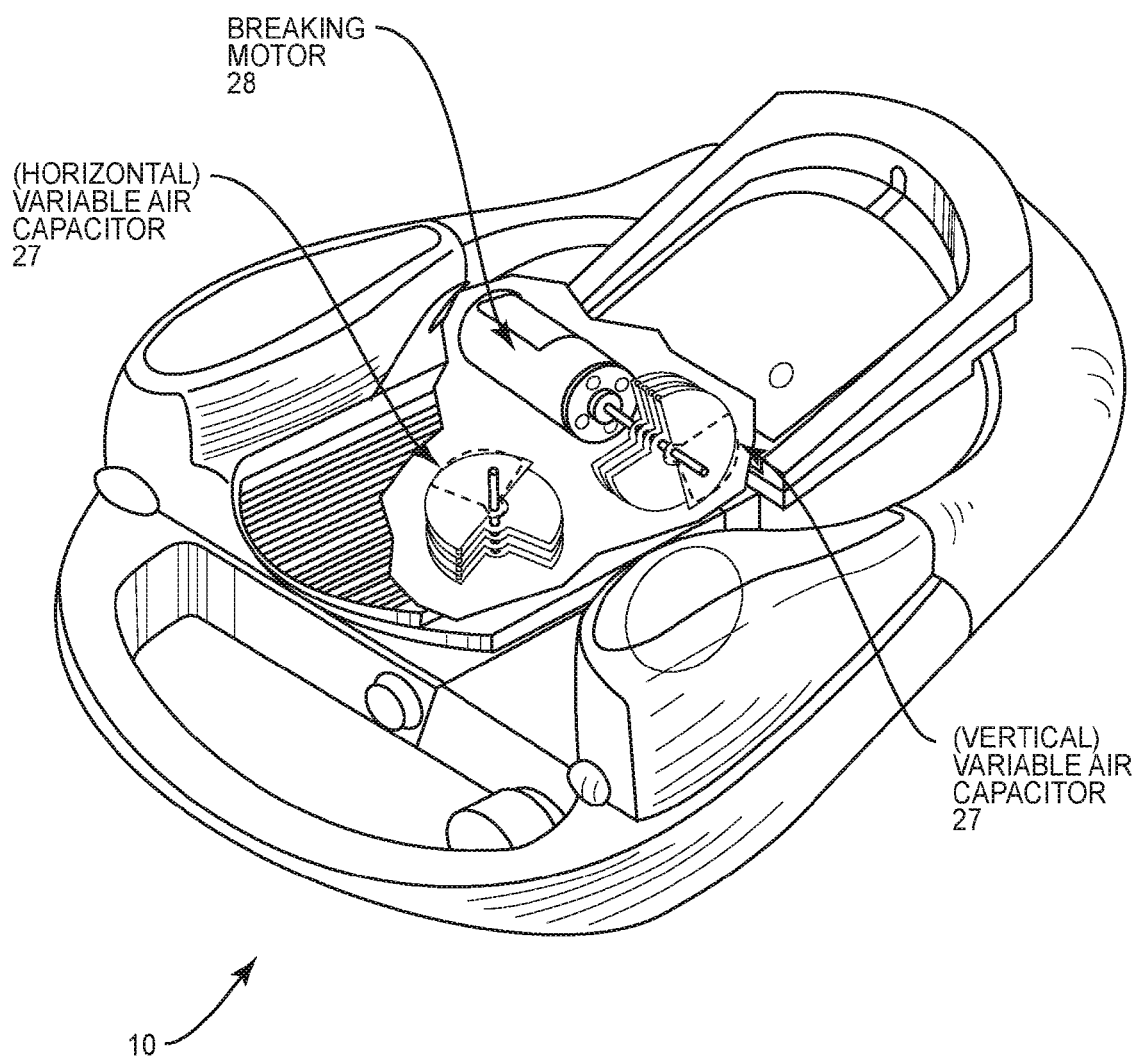
FIG. 2B provides a cut-away view of an example footswitch assembly, illustrating included variable air capacitors.

Operatively coupled to the foot pedal or tiltable treadle 16 via at least one variable air capacitor 27 is a capacitance-sensing controller circuit 22, as illustrated in the cross section provided by FIG. 2A and cutaway view shown in FIG. 2B. Capacitance-sensing controller circuit 22 is operative to translate the angular or pitch position of the foot pedal or treadle 16, which is tiltable at least with respect to a horizontal plane or to a neutral or home plane, from a mechanical input based on the movement of the operator's foot into an electrical signal. Thus, the pitch 15 movement of the foot pedal or tiltable treadle 16, typically in a downward direction, provides a control input.

The foot pedal or treadle 16 is coupled to the capacitance-sensing controller circuit 22 via at least one variable air capacitor 27. In the example shown in FIG. 2B, the variable air capacitors 27 are mechanically controlled rotary capacitors, comprising a series of metal plates arranged on a shaft such that angular rotation of the shaft varies an overlap between adjacent plates, thus varying the capacitance of the device. FIG. 2B illustrates an embodiment with two such variable air capacitors 27, with a first one arranged so that the capacitance is varied by rotational motion in the horizontal plane, and a second one arranged to capture rotational motion in a vertical plane. It will be appreciated that vertical air capacitor 27, i.e., a variable air capacitor arranged so that its capacitance is varied by rotational (or, optionally linear) motion in the vertical plane, can be mechanically coupled to the tilting foot pedal 16 so that the tilting of the foot pedal 16 rotates the shaft of the vertical air capacitor 27. The shaft of the vertical air capacitor 27 may form part or all of an axle around which the foot pedal 16 rotates, in some embodiments. In others, the shaft of the vertical variable air capacitor 27 may be mechanically coupled to a rotating axle or pivot point of the tilting foot pedal by some other means, e.g., by a simple pully system or via one or more gears. In still other embodiments, an alternative structure for vertical variable air capacitor may be used—for example, a mechanically controlled variable air capacitor may be configured to capture linear motion, e.g., using two sets of parallel plates that translate, or slide, with respect to one another. Such a capacitor may be mechanically coupled to the foot pedal 16 so that the vertical motion of the pedal at some distance from the pivot point causes translation of the variable air capacitor, varying its capacitance.

The example embodiment shown in FIG. 2B further includes a horizontal variable air capacitor 27, i.e., a variable air capacitor arranged so that its capacitance is varied by rotational (or, optionally linear) motion in the horizontal plane. Foot pedal 16 and, if present, heel cup 18, may in some embodiments be coupled to the base of footswitch 10 with a vertically arranged pivot point, so as to permit rotational motion of foot pedal 16 in the horizontal plane. This rotational motion in the horizontal plane is coupled to the capacitance-sensing controller circuit 22 via the horizontal variable air capacitor 27. For example, the shaft of the horizontal air capacitor 27 may form part or all of a horizontally arranged axle or pivot point around which the foot pedal 16 rotates in the horizontal plane, in some embodiments. In others, the shaft of the horizontal variable air capacitor 27 may be mechanically coupled to this rotating axle or pivot point by some other means, e.g., by a simple pully system or via one or more gears. Once again, in other embodiments an alternative structure for vertical variable air capacitor may be used, such as a mechanically controlled variable air capacitor configured to capture linear motion in the horizontal plane, e.g., using two sets of parallel plates that translate, or slide, with respect to one another. Such a capacitor may be mechanically coupled to the foot pedal 16 so that the horizontal motion of the pedal at some distance from the vertical pivot point causes translation of the variable air capacitor, varying its capacitance.

Also shown in FIG. 2B is a braking motor 28, which in the illustrated example is a brushed DC motor mechanically coupled to the shaft or axle that provides the pivot point for foot pedal 16. In the illustrated embodiment, the vertical air capacitor 27 and braking motor 28 have a common shaft, which may also serve as the pivot point for tiltable foot pedal 16. Braking motor 28 is configured as a generator, with a resistive load that may be fixed, in some embodiments, or variable, in others. Braking motor 28 effectively operates as an eddy current brake mechanism, providing mechanical resistance to the tilting of foot pedal 16, thus providing tactile feedback to the operator, and improving the operator's control. Note that while the embodiment shown in FIG. 2B includes a braking motor 28 only coupled to the vertical motion of foot pedal 16, a braking motor 28 could be instead or additionally arranged to provide mechanical resistance to rotation of foot pedal 16 in the horizontal plane.

Figure 3:
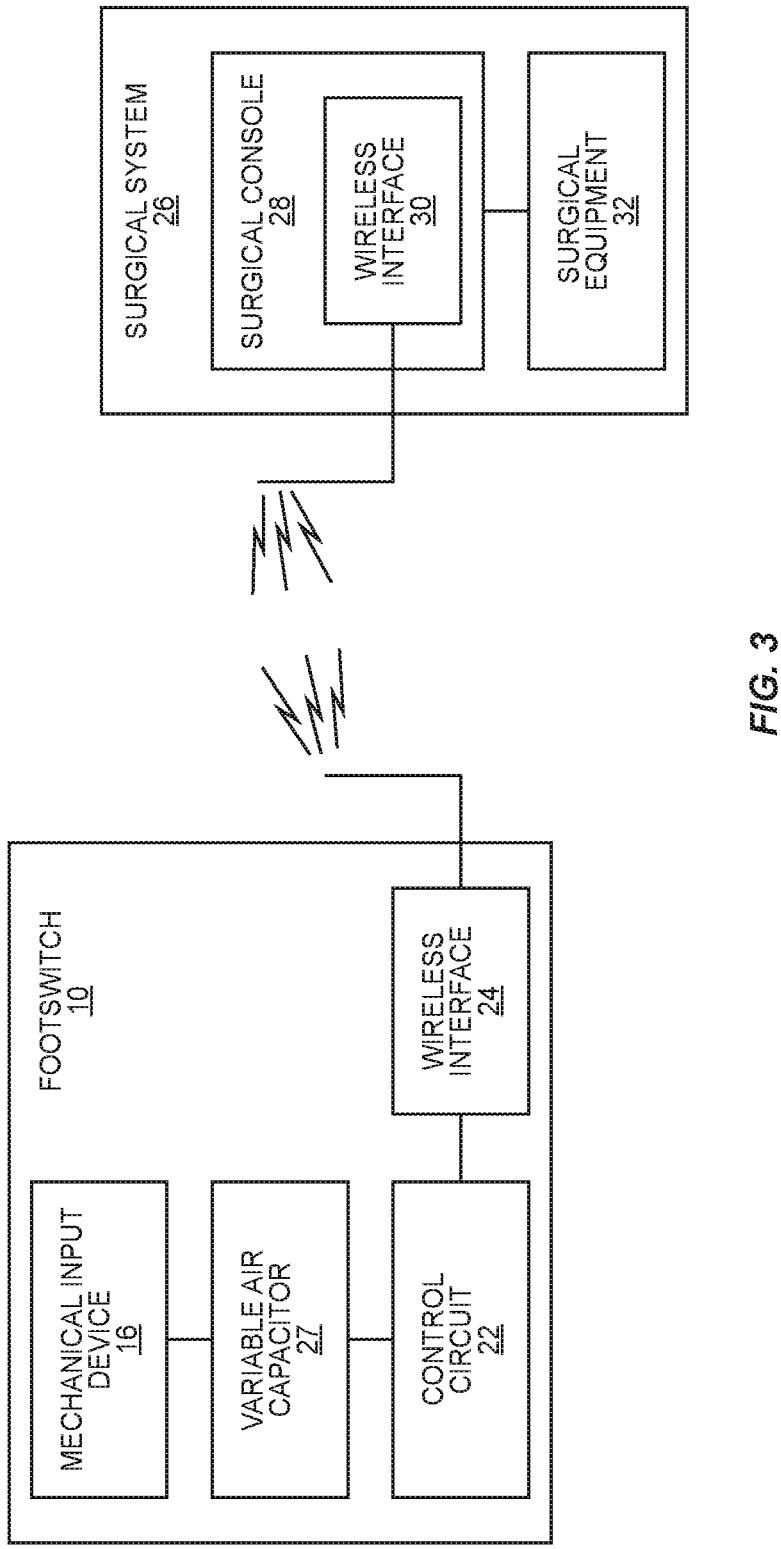
FIG. 3 provides a functional diagram illustrating how an example footswitch wirelessly couples to a surgical system.

FIG. 3 provides a functional diagram that illustrates how the footswitch 10 wirelessly couples to a surgical system 26. Footswitch 10 contains a mechanical input device such as pedal 16 that couples to capacitance-sensing controller circuit 22 via air variable capacitor 27, in order to produce a control signal that is provided to wireless interface 24. More particularly, it will be appreciated that because the charge stored by a capacitor is equal to its capacitance times the voltage at the capacitor's terminals, a varying capacitance, as caused by tilting of the foot pedal 16, will result in a varying profile of voltage versus charge. This principle can be used to design any number of very low-current circuits for directly or indirectly sensing the capacitance, such as a circuit that provides a known current to the variable air capacitor for a short, fixed period of time, while measuring the change in voltage across the capacitor's terminals. The sensed capacitance across the range of motion of the foot pedal 16 can be linearized, e.g., using a simple look-up table, to provide a measure of the foot pedal 16's position (e.g., in terms of its angle) at any given time. Changes in the pedal's position can then be detected and converted into a digital signal for relaying wirelessly to the surgical system 26. In some embodiments, a mechanically activated electrical switch may be arranged in footswitch 10 so that it is activated when foot pedal 16 is at one end of its motion, to provide a "home" position—capacitance-sensing controller circuit 22 in some of these embodiments may be configured to detect this activation and calibrate its conversion of sensed capacitance to detected pedal position, e.g., by linear shifting of the capacitance-to-pedal-position lookup table values. In some embodiments, a second mechanically activated electrical switch may be arranged so that it is activated when foot pedal is at an opposite extreme of its motion—again, capacitance-sensing controller circuit 22 ins some embodiments may detect this activation and calibrate its conversion, e.g., by combining a linear shift of the capacitance-to-pedal-position lookup table values with a multiplicative scaling of the sensed capacitance value.

Wireless interface 24 is operable to establish a wireless communication pathway between footswitch 10 and surgical system 26. Specifically, wireless interface 24 communicatively couples to wireless interface 30 of surgical console 28. Thus, the control signal(s) produced by capacitance-sensing controller circuit 22 are able to be communicated to surgical console 28 via the wireless pathway. Surgical console 28 is operable to direct surgical equipment 32 based on the control signal(s) that are wirelessly relayed from the footswitch to the surgical console. Wireless interface 24 may be implemented, for example, using low-power wireless transmitter circuitry, where wireless interface 30 comprises a corresponding receiver circuit. A number of ultra-low-power wireless link technologies are commercially available, including standardized solutions known as Bluetooth® Low-Energy, Sub-1 GHz, 6LoWPAN, Zigbee®, and RF4CE. Of course, a customized wireless link technology may also be used.

Figure 4:
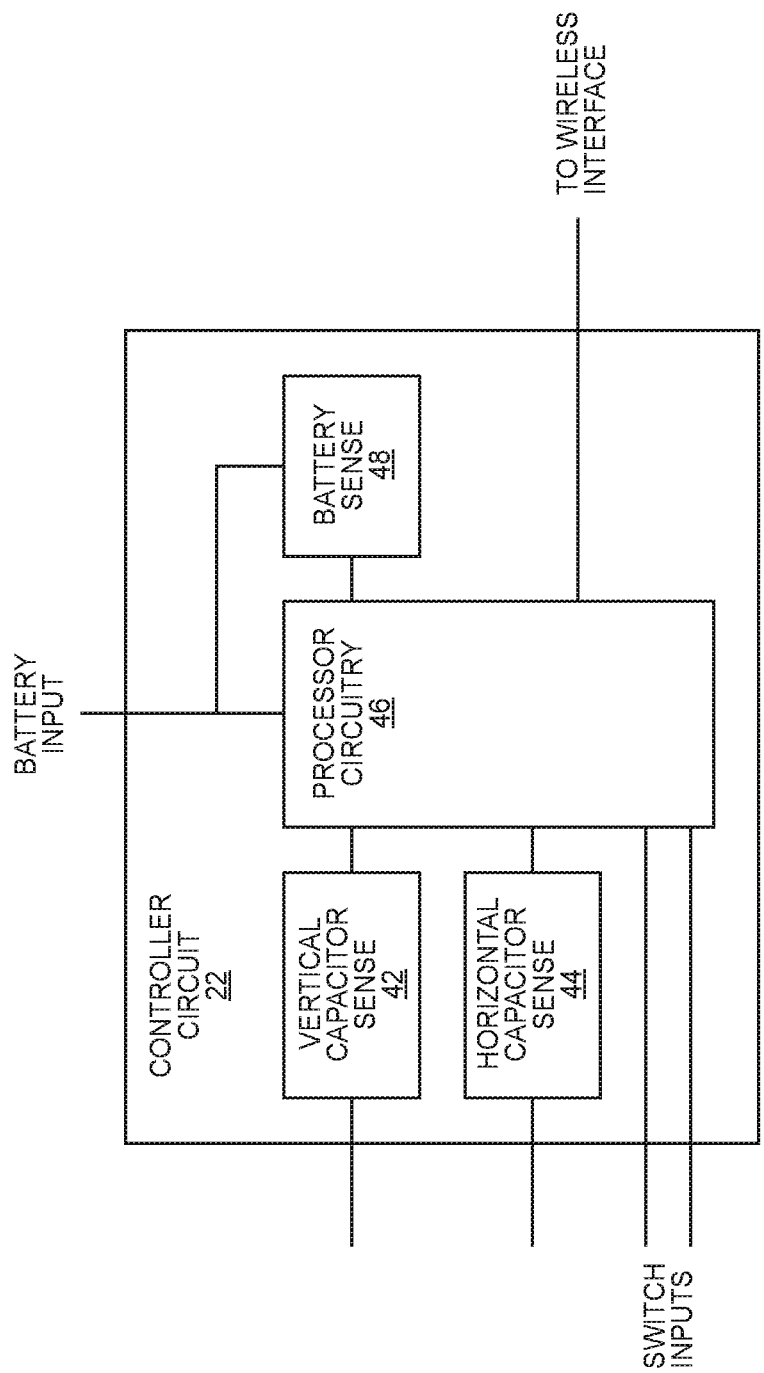
FIG. 4 is a schematic diagram illustrating an example capacitance-sensing controller circuit.

FIG. 4 illustrate an example capacitance-sensing controller circuit 22. Capacitance-sensing controller circuit 22 includes a vertical capacitor sense circuit 42 and may, in some embodiments, further comprise a horizontal capacitor sense circuit 44. These circuits may each comprise, for example, a low-power current source that is selectively activated by processor circuitry 46 to inject charge into the respective variable air capacitor 27, and a voltage measurement circuit to measure a voltage or change in voltage at the terminal of the respective air capacitor 27. A low-power voltage measurement circuit may comprise an operational amplifier with its output coupled to an ultra-low power analog-to-digital converter, for example. The example capacitance-sensing controller circuit 22 shown in FIG. 4 provides for several switch inputs, in addition to the inputs from the variable air capacitors—these switch inputs may be coupled to one or more mechanical switches that indicate the end of a range of motion for pedal 16, in some embodiments, and/or may be coupled to one or more mechanical switches that can be operator activated, such as the side switches 20 shown in FIG. 1.

Referring back to FIG. 4, capacitance-sensing controller circuit 22 further includes a battery sense circuit 48, connected to the battery input to capacitance-sensing controller circuit 22. Battery sense circuit 48 selectively monitors the voltage of the externally connected battery, under the control of controller 46, and may again be a low-power voltage measurement circuit. A sagging battery voltage can be detected by controller 46, using battery sense circuit 48, so that a low battery warning can be wireless relayed to the surgical system 26. When capacitance-sensing controller circuit 22 is designed using ultra-low power consumption design principles, this low battery warning may be transmitted weeks, or even months, before a replacement is necessary, giving surgical staff plenty of time to change the consumer batteries in the footswitch 10.

Processor circuitry 46 may comprise a low-power microcontroller or microprocessor, executing program code stored in firmware or flash memory, for example. Processor circuitry 46 may instead or additionally comprise customized digital logic. In various embodiments, processor circuitry 46 may comprise a single processing device or a plurality of processing devices, where such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. Memory coupled to the microprocessor or control circuit may be a single memory device or a plurality of memory devices. Such a memory device may be a read-only memory, random access memory, volatile memory, non-volatile memory, static memory, dynamic memory, flash memory, cache memory, and/or any device that stores digital information, such as a look-up table for conversion of sensed capacitance to pedal position. Note that when the microprocessor or control circuit implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory stores, and the microprocessor or control circuit executes, operational instructions corresponding to at least some of the steps and/or functions illustrated and described herein.

In particular, processor circuitry 46 is configured, e.g., with appropriate program code, to monitor the capacitances of one or more variable air capacitors 27, where the varying capacitance of these variable air capacitors 27 is indicative of different positions or orientations of movable pedal 16 in footswitch 16. Processor circuitry 46 may further monitor one or more switch inputs, as well as an input from a battery sense circuit 48; processor circuitry 46 may convert these monitored inputs, or changes in these inputs, to control signals (such as a low-battery warning signal) for relaying to surgical system 26. Likewise, processor circuitry 46 is configured to convert the sensed capacitance(s) to one or more control signals, for relaying to a surgical system 26. Processor circuitry 46 may linearize the sensed capacitances, in some embodiments, e.g., using a lookup table; in some embodiments processor circuitry 46 may shift or scale a linearized version of the sensed capacitances, based on one or more switch inputs indicating corresponding end-points in the pedal's movement.

In some embodiments, only a single variable air capacitor is used. In others there may be two. Thus, in some embodiments, processor circuitry 46 may form and relay first and second control signals, corresponding to first and second variable air capacitor capacitances, respectively, where the first and second variable air capacitor capacitances correspond to pedal movement in first and second planes, respectively. In other embodiments, processor circuitry 26 may relay a composite control signal based on both capacitances.

In summary, the present invention provides a surgical footswitch 10 that comprises a base, a pedal 16, a capacitance-sensing controller circuit 22 coupled to pedal 16 via one or more variable air capacitors 27, and a wireless interface 24. The pedal 16 mounts upon the base and can pivot in at least one plane. The capacitance-sensing controller circuit 22 couples to pedal 16 via at least one variable air capacitor 27. As pedal 16 pivots, the capacitance-sensing controller circuit 22 senses the capacitance of variable air capacitor 27, which varies according to the pedal's position, and converts the capacitance into an indication of the pedal's position or an indication of a change in the pedal's position. This indication represents or is used to form a control signal. The wireless interface 24 couples to the capacitance-sensing controller circuit 22 to receive the control signal. The wireless interface 24 also couples surgical footswitch 10 to surgical console 28 operable to control and direct surgical equipment 32. The wireless interface 24 passes the control signal from the capacitance-sensing controller circuit 22 to the surgical console 28, which then directs the surgical equipment 32 based on the control signal. This wireless interface 24 eliminates the tangle of wires or tethers common in the prior art and which may be a hazard in the surgical theater.

The pedal positioning techniques described herein may be used to provide for an extended battery life, using inexpensive consumer batteries. Battery status (voltage) can be transmitted to the surgical console along with treadle and footswitch positions, providing surgical staff with an early low battery warning long before a replacement is necessary. The battery compartment of the footswitch can be made such that the staff can easily change the batteries. An additional advantage provided by the use of replaceable non-rechargeable batteries stems from the fact that rechargeable batteries have a charge count lifetime, i.e., the batteries can only be charged a finite number of times before they fail. This failure can mean costly repairs to the end user when the internal battery fails and may result in the device being out of service for an extended period of time. The elimination of a charging system also reduces the cost of the surgical apparatus.

Although the present invention is described in detail, it should be understood that various changes, substitutions and alterations can be made hereto without departing from the spirit and scope of the invention as described by the appended claims.

The invention claimed is:

1. A surgical footswitch, comprising:
a base;
a pedal mounted to the base;
first and second variable air capacitors mechanically coupled to the pedal, such that rotation of the pedal in a vertical plane is operative to vary the capacitance of the first variable air capacitor and movement of the pedal in a horizontal plane is operative to vary the capacitance of the first variable air capacitor;
a capacitance-sensing controller circuit electrically connected to the first and second variable air capacitors and is configured to produce first and second control signals or a composite control signal based on the respective capacitances of the first and second variable air capacitors, such that the control signal reflects a position of the pedal or a change in the position of the pedal; and
a wireless interface electrically connected to the capacitance-sensing controller circuit and configured to wirelessly relay the first and second control signals or the composite control signal to the surgical console to a surgical console.

2. The surgical footswitch of claim 1, further comprising an eddy current brake mechanism mechanically coupled to the pedal, such that the movement of the pedal is operative to cause the eddy current brake mechanism to generate a mechanically resistive force opposing the movement.

3. The surgical footswitch of claim 2, wherein the eddy current brake mechanism is a brushed direct-current (DC) motor.

4. The surgical footswitch of claim 3, wherein the eddy current brake mechanism comprises an electrically variable load resistance.

5. The surgical footswitch of claim 1, further comprising one or more non-rechargeable batteries configured to power the capacitance-sensing controller circuit.

6. The surgical footswitch of claim 5, wherein the capacitance-sensing controller circuit further comprises a battery sense circuit configured to monitor a voltage level of the one or more non-rechargeable batteries, and wherein the capacitance-sensing controller circuit is configured to relay a low-battery signal to the surgical console, via the wireless interface, responsive to detecting that the monitored voltage level is below a predetermined threshold level.

* * * * *